US012642781B2

(12) United States Patent
Stamenov et al.

(10) Patent No.: US 12,642,781 B2
(45) Date of Patent: Jun. 2, 2026

(54) ADENOMYOSIS ASSOCIATED INFERTILITY AND HDAC INHIBITORS

(71) Applicant: NADEZHDA REPRODUCTIVE SCIENCE OOD, Sofia (BG)

(72) Inventors: Gueorgui Stamenov, Sofia (BG); Mariyana Eneva, Sofia (BG)

( * ) Notice: Subject to any disclaimer, the term of this patent is extended or adjusted under 35 U.S.C. 154(b) by 713 days.

(21) Appl. No.: 17/998,076

(22) PCT Filed: Apr. 13, 2021

(86) PCT No.: PCT/EP2021/059584
§ 371 (c)(1),
(2) Date: Nov. 7, 2022

(87) PCT Pub. No.: WO2021/223966
PCT Pub. Date: Nov. 11, 2021

(65) Prior Publication Data
US 2023/0125269 A1 Apr. 27, 2023

(30) Foreign Application Priority Data

May 5, 2020 (GB) ...................................... 2006646

(51) Int. Cl.
*A61K 31/19* (2006.01)
*A61P 15/00* (2006.01)

(52) U.S. Cl.
CPC .............. *A61K 31/19* (2013.01); *A61P 15/00* (2018.01)

(58) Field of Classification Search
CPC ........ A61K 31/19; A61K 9/0034; A61K 9/08; A61P 15/08
See application file for complete search history.

(56) References Cited

U.S. PATENT DOCUMENTS

2007/0287676 A1* 12/2007 Guo ..................... C12Q 1/6883
435/193

FOREIGN PATENT DOCUMENTS

WO 2005020880 A2 3/2005

OTHER PUBLICATIONS

Farquhar, C., & Brosens, I. (2006). Medical and surgical management of adenomyosis. Best Practice Research Clinical Obstetrics Gynaecology, 20(4), 603-616. doi:10.1016/j.bpobgyn.2006.01.012.

Guo, S., Mao, X., Ma, Q., & Liu, X. (2013). Dysmenorrhea and its severity are associated with increased uterine contractility and overexpression of oxytocin receptor (OTR) in women with symptomatic adenomyosis. Fertility and Sterility, 99(1), 231-240. doi:10.1016/j.fertnstert.2012.08.038.

Li, J., Chung, J. P., Wang, S., Li, T., & Duan, H. (2018). The investigation and management of adenomyosis in women who wish to improve or preserve fertility. BioMed Research International, 2018, 1-12. doi:10.1155/2018/6832685.

(Continued)

*Primary Examiner* — San Ming R Hui
(74) *Attorney, Agent, or Firm* — Dunlap Bennett & Ludwig PLLC; Anna L. Kinney

(57) ABSTRACT

The present invention relates to new uses and methods of treatment. More specifically, the invention relates to new uses of histone deacetylase inhibitors (HDACI) such as valproic acid (VPA), for enhancing in vitro fertilization (IVF) in patients suffering with adenomyosis associated infertility.

20 Claims, 1 Drawing Sheet

A graph showing reduction of diameter of adenomyosis lesions

(56) References Cited

OTHER PUBLICATIONS

Liu, X., & Guo, S. (2008). A pilot study on the off-label use of valproic acid to treat adenomyosis. Fertility and Sterility, 89(1), 246-250. doi:10.1016/j.fertnstert.2006.11.009.

Liu, X., & Guo, S. (2011). Valproic acid alleviates generalized hyperalgesia in mice with induced adenomyosis. Journal of Obstetrics and Gynaecology Research, 37(7), 696-708. doi:10.1111/j.1447-0756.2011.01655.x.

Liu, X., Yuan, L., & Guo, S. (2010). Valproic acid as a therapy for adenomyosis: A comparative case series. Reproductive Sciences, 17(10), 904-912. doi:10.1177/1933719110373807.

Mao, X., Wang, Y., Carter, A. V., Zhen, X., & Guo, S. (2011). The retardation of myometrial infiltration, reduction of uterine contractility, and alleviation of generalized hyperalgesia in mice with induced adenomyosis by levo-tetrahydropalmatine (L-THP) and Andrographolide. Reproductive Sciences, 18(10), 1025-1037. doi:10.1177/1933719111404610.

Vannuccini, S., Luisi, S., Tosti, C., Sorbi, F., & Petraglia, F. (2018). Role of medical therapy in the management of uterine adenomyosis. Fertility and Sterility, 109(3), 398-405. doi:10.1016/j.fertnstert.2018.01.013.

International Search Report and Written Opinion; PCT/EP2021/059584; Mailed Jul. 5, 2021.

Great Britain Search Report; GB2006646.0; Jan. 11, 2021.

* cited by examiner

A graph showing reduction of diameter of adenomyosis lesions
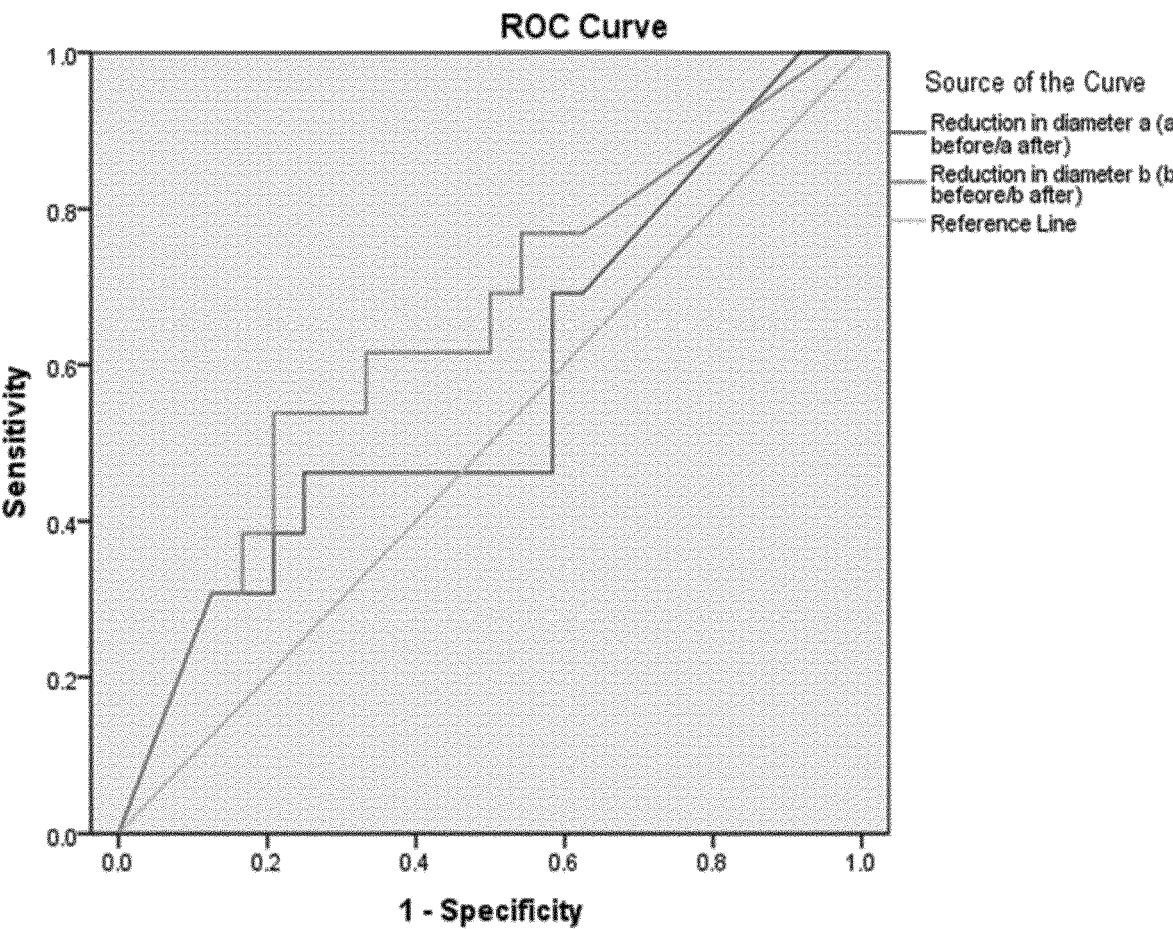
Diagonal segments are produced by ties.

ADENOMYOSIS ASSOCIATED INFERTILITY AND HDAC INHIBITORS

The present invention relates to new uses and methods of treatment. More specifically, the invention relates to new uses of histone deacetylase inhibitors (HDACI) such as valproic acid (VPA), for enhancing in vitro fertilization (IVF) in patients suffering with adenomyosis associated infertility.

BACKGROUND

The reference or discussion of an apparently prior-published document should not necessarily be taken as an acknowledgement or recognition that that document is part of the state of the art or that it constitutes common general knowledge for the present invention.

The clinical condition Adenomyosis could generally be described as a benign uterine disorder or nonneoplastic condition, in which ectopic endometrial glands and stroma pathologically surrounded by hyperplastic smooth muscle within the myometrium (McCluggage et al., 2009). Behind this description lies one of the most enigmatic and difficult to effectively treat gynaecologic diseases. Adenomyosis is a heterogeneous gynaecologic condition (or a series of different types of lesions e.g. polyps and cysts, and symptoms) with a range of clinical presentations adversely affecting 5-70% of women in the reproductive period of life. Lesions which are associated with Adenomyosis may vary in size, coloration, contour and surface.

Adenomyosis frequently coexists with uterine leiomyomas and endometriosis. Women affected by adenomyosis may present with abnormal uterine bleeding (AUB), dysmenorrhea, dyspareunia, or infertility but one third of them are asymptomatic (Peric et al., 2006). For many years, adenomyosis remained a histopathological diagnosis made mainly after hysterectomy in perimenopausal women with heavy menstrual bleeding (HMB) or pelvic pain. Over the last decade, adenomyosis has also become a condition identified in young fertile-age women thanks to the recent advancements in imaging techniques, even though a shared definition and classification are unsynchronised (Van den Bosch et al., 2018).

Despite some improvements of diagnostic tools, the awareness of the condition is still poor. Furthermore, in some patients, adenomyosis coexists with other gynecological conditions, such as endometriosis and uterine fibroids. The physio-pathological mechanisms, involving sex steroid hormone aberrations, inflammation, fibrosis and neuroangiogenesis, are not that well understood or characterised. At present there are no international guidelines which can be followed by medical practitioners for surgical or medical treatment of adenomyosis and this will be of utmost immediate importance and certainly in the future as the disease requires pain and bleeding control, fertility preservation and eventual pregnancy.

Current Medical Treatment

The standard treatment of adenomyosis is hysterectomy while conservative therapies include for example suppressive hormonal treatments.

At present, there is no medical therapy or intervention which is capable of treating the symptoms of adenomyosis while still allowing patients to conceive safely. Many studies investigate the reproductive outcome after assisted reproductive technologies (ART) in women with adenomyosis, reporting that adenomyosis causes infertility and there are lower pregnancy rates in women with adenomyosis who undergo in vitro fertilization (IVF).

Traditionally, adenomyosis is more often diagnosed in later reproductive age; which, coupled with the tendency for women in modern industrial societies to postpone motherhood till their late thirties and early forties, results in an increasing number of infertility cases related to adenomyosis. The financial and social costs related to repeated IVF failures of patients in advanced reproductive age, compromised by adenomyosis, are significant and rising.

Developing new and improved approaches and disease management strategies to effectively treat adenomyosis, while preserving women's fertility is a pressing problem with increasing medical and social significance. Therefor there are definite and urgent needs to develop new methods for treating adenomyosis, increase fertility and success of conception such as for example following IVF.

SUMMARY

This disclosure relates to the field of assisted reproductive technologies such as IVF, intrauterine insemination (IUI) and, in particular, to a method of enhancing implantation of embryos to a patient (i.e. a woman or other female animal). More particularly, disclosed herein is a method of enhancing in vitro fertilization (IVF) in a patient suffering with adenomyosis associated infertility. The term "patient" is used interchangeably with the term "subject".

In one aspect, there is provided a method of enhancing in vitro fertilization (IVF) in a subject suffering with adenomyosis associated infertility, the method comprising administering a therapeutically effective amount of HDACI, derivatives and/or salts thereof.

In some embodiments, there is provided a method of enhancing in vitro fertilization (IVF) in a subject suffering with adenomyosis associated infertility, wherein the therapeutically effective amount is achieved by a regimen of administration of HDACI, derivatives and/or salts thereof.

In some embodiments, the regimen of administration of HDACI, derivatives and/or salts thereof is carried out using methods known in the art.

In some embodiments, there is provided a method of enhancing in vitro fertilization (IVF) in a subject suffering with adenomyosis associated infertility, wherein the regimen comprises a combination of intralesional and peroral administration of HDACI, derivatives and/or salts thereof.

In some embodiments, the regimen comprises one or more intralesional administrations of HDACI, derivatives and/or salts thereof.

In some embodiments, the regimen comprises two or more intralesional administrations. In some embodiments, the regimen comprises three or more intralesional administrations.

In some embodiments, the regimen comprises four or more intralesional administrations.

In some embodiments the regimen comprises two intralesional administrations.

In some embodiments, the intralesional administration of HDACI, derivatives and/or salts thereof is carried out using methods known in the art.

In some embodiments, the intralesional administration is carried out using hysteroscopy.

In some embodiments, the intralesional administration is carried out using hysteroscopy or transvaginal ultrasound-guided needle.

In some embodiments, the intralesional administration is carried out using transvaginal ultrasound-guided needle selected from the group comprising 18G, 21G, 23G, 25G or 30G.

It will be appreciated by those skilled in the art that the amount or dose of HDACI, derivatives and/or salts thereof required in the present methods will vary with the nature or severity of the condition being treated, the type of the adenomyotic lesions, the age, weight and the overall condition of the patient, and will be ultimately at the discretion of the attendant physician. The amount or dose of HDACI, derivatives and/or salts thereof is preferably pharmaceutically relevant for the intended use and desired outcome such as enhancing in vitro fertilization in a patient suffering with adenomyosis associated infertility or reduction of adenomyosis lesions.

In general however, a dose of HDACI, derivatives and/or salts thereof employed in the present methods will typically be in the range of about 2 to about 1000 mg/ml per administration, dependent upon the route of administration.

The dose may conveniently be presented in a single dose or as divided doses administered at appropriate intervals, for example as two, three, four or more sub-doses per day or per administration.

In some embodiments, for intralesional administration a dose will typically be in the range of about 1 to 500 mg/ml, about 5 to 250 mg/ml, about 10 to 200 mg/ml, about 20 to 150 mg/ml, about 50 to 100 mg/ml per administration. In some embodiment the dose of intralesional administration is 100 mg/ml per administration.

In some embodiments, the regimen comprises one or more peroral administrations of HDACI, derivatives and/or salts thereof. In some embodiments, the regimen comprises two or more peroral administrations. In some embodiments, the regimen comprises three or more intralesional administrations. In some embodiments, the regimen comprises four or more reporal administrations. In some embodiments, the regimen comprises two peroral administrations of HDACI, derivatives and/or salts thereof.

In some embodiments, for oral administration a daily dose will typically be within the range of about 10 to 1500 mg, about 50 to 1250 mg, about 100 to 1000 mg, about 200 to 750 mg. In some embodiments, the oral administration daily dose is 1000 mg.

In some embodiments, there is provided a method of enhancing in vitro fertilization (IVF) in a subject suffering with adenomyosis associated infertility, the method comprising a regimen of:
- a. a first intralesional administration of HDACI, derivatives and/or salts thereof;
- b. a first peroral administration of HDACI, derivatives and/or salts thereof lasting for about three months (90 days) after step a):
- c. a second intralesional administration of HDACI, derivatives and/or salts thereof; and
- d. a second peroral administration of HDACI, derivatives and/or salts thereof lasting for about one month (30 days) after step c); followed by
- e. standard IVF.

In some embodiments, there is provided a method of enhancing in vitro fertilization (IVF) in a subject suffering with adenomyosis associated infertility, the method comprising a regimen of intralesional administration and peroral administration of HDACI, derivative and/or salts thereof which leads to regression of adenomyosis lesions.

In some embodiments, the present method alters the frequency of occurrence of adenomyosis lesions.

In some embodiments, the present method reduces the frequency of occurrence of the adenomyosis lesions.

In some embodiments, there is provided a method of enhancing in vitro fertilization (IVF) in a subject suffering with adenomyosis associated infertility, the method comprising a regimen of intralesional administration and peroral intake of HDACI, derivative and/or salts thereof, where the frequency of occurrence of the lesions is reduced by at least 0.5%, at least 1%, at least 5%, at least 10%, at least 20%, at least 30%, at least 40%, at least 50%, at least 60%, at least 70%, at least 80%, at least 90%, at least 100%, at least 120%, at least 135%, at least 140%, at least 150, at least 160%, at least 170%, at least 180%, at least 190%, at least 200%, at least 210%, at least 220%, at least 230%, at least 250% or more.

In some embodiments, the present method alters the size of the adenomyosis lesions. As used herein the term "size" refers to the diameter, circumference, contour or surface of the adenomyosis lesion. In some embodiments, there is provided a method for treating adenomyosis, the method comprising a regimen of intralesional administration and peroral intake of HDACI, derivative and/or salts thereof, where the size e.g. diameter, circumference, contour or surface, of the lesions is reduced.

In some embodiments, there is provided a method of enhancing in vitro fertilization (IVF) in a subject suffering with adenomyosis associated infertility, the method comprising a regimen of intralesional and peroral administration of HDACI, derivative and/or salts thereof, where the lesions are reduced by at least 0.5%, at least 1%, at least 5%, at least 10%, at least 20%, at least 30%, at least 40%, at least 50%, at least 60%, at least 70%, at least 80%, at least 90%, at least 100%, at least 120%, at least 135%, at least 140%, at least 150, at least 160%, at least 170%, at least 180%, at least 190%, at least 200%, at least 210%, at least 220%, at least 230%, at least 250% or more.

In some embodiments, ultrasound imaging technique is used to determine adenomyotic lesions.

In some embodiments, ultrasound imaging technique is used to determine the type and size of the adenomyotic lesions before the method.

In some embodiments, ultrasound imaging technique is used to determine the type and size of the adenomyotic lesions during the method.

In some embodiments, ultrasound imaging technique is used to determine the type and size of the adenomyotic lesions after the method.

In some embodiments, ultrasound imaging technique is used to determine changes in the adenomyotic lesions as a consequence of the method.

In some embodiments, there is provided a method of enhancing in vitro fertilization (IVF) in a subject suffering with adenomyosis associated infertility, where the method leads to at least 50% remission of adenomyosis, at least 55% remission of adenomyosis, at least 60% remission of adenomyosis, at least 65% remission of adenomyosis, at least 70% remission of adenomyosis, at least 75% remission of adenomyosis, at least 80% remission of adenomyosis, at least 81% remission of adenomyosis, 82%, 83%, 84%, 85%, 86%, 87%, 88%, 89%, 90%, 91%, 92%, 93%, 94%, 95%, 96%, 97%, 98%, 99% or 100% remission of adenomyosis. In some embodiments, there is provided a method for treating adenomyosis, wherein the treatment leads to full remission of adenomyosis.

In some embodiments, there is provided a method of enhancing in vitro fertilization (IVF) in a subject suffering with adenomyosis associated infertility, wherein the method leads to an enhancement in embryo retention.

In some embodiments, there is provided a method of enhancing in vitro fertilization (IVF) in a subject suffering with adenomyosis associated infertility, wherein the method leads to an increase of success of conception following IVF.

In some embodiments, there is provided a method of enhancing in vitro fertilization (IVF) in a subject suffering with adenomyosis associated infertility, wherein the method leads to at least 0.5%, at least 1%, at least 2%, at least 3%, at least 4%, at least 5%, at least 6%, at least 7%, at least 8%, at least 9%, at least 10% or more, increase in a successful conception.

The method is also applicable for women wanting to improve their prospects of pregnancy through natural conception.

In some embodiments, there is provided a method of enhancing in vitro fertilization in a patient suffering with adenomyosis associated infertility, wherein the HDACI, derivative and/or salts thereof, comprises valproic acid (VPA), derivative and/or salts thereof. In some embodiments, the VPA salt is sodium valproate.

In some embodiments, the intralesional administration dose of VPA, derivative and/or salt thereof will typically be in the range of about 1 to 500 mg/ml, about 5 to 250 mg/ml, about 10 to 200 mg/ml, about 20 to 150 mg/ml, about 50 to 100 mg/ml per intralesional administration. In some embodiment the VPA intralesional administration dose is 100 mg/ml per administration. In some embodiments the intralesional administration dose of sodium valproate is 100 mg/ml.

In some embodiments, the oral administration daily dose of VPA, derivative and/or salt thereof will typically be within the range of about 10 to 1500 mg, about 50 to 1250 mg, about 100 to 1000 mg, about 200 to 750 mg. In some embodiments, the oral administration daily dose of VPA, derivative and/or salt thereof is 1000 mg. In some embodiments, the oral administration daily dose of sodium valproate is 1000 mg.

BRIEF DESCRIPTION OF THE DRAWINGS

FIG. 1 Depicts a graph showing reduction of diameter of adenomyosis lesions in patients who gave birth following treatment using the method of the present invention as compared to those who did not.

DETAILED DESCRIPTION

Throughout this disclosure, various scientific publications, patents and published patent specifications are referenced by an identifying citation. The disclosures of these publications, patents and published patent specifications are hereby incorporated by reference into the present disclosure to more fully describe the state of the art to which this disclosure pertains.

As used herein, certain terms may have the following defined meanings.

As used in the specification and claims, the singular form "a," "an" and "the" include singular and plural references unless the context clearly dictates otherwise. For example, the term "HDACI" includes a single HDACI or plurality, as well as derivatives and/or salts thereof, including mixtures thereof.

All numbers or numerals as used herein that indicate amounts, ratios of materials, physical properties of materials, and/or use are to be understood as modified or qualified by the term "about," except as otherwise explicitly indicated.

As used herein, the term "about" includes the recited number or number and +/−10% from the recited numeral or number. By way of non-limiting example, the term "about ten (10)" would encompass nine (9) to eleven (11) or 9-11.

This disclosure relates to the field of assisted reproductive technologies such as IVF and intrauterine insemination (IUI) and, in particular, to a method of enhancing implantation of embryos to a patient (i.e. a woman or other female animal). More particularly, disclosed herein is a method of enhancing in vitro fertilization (IVF) in a patient suffering with adenomyosis associated infertility.

While the emphasis of the present disclosure resides with women, those skilled in the art will readily recognise that the methods (the regimen of administration of HDACI, derivatives and/or salts thereof) disclosed herein are also applicable to other non-human female subjects (i.e. other female animals) such as, for example, livestock (e.g. cattle, horses and sheep), exotic animals (e.g. pandas, big cats such as tigers, lions and pumas, elephants and similar animals) and companion animals (such as dogs and cats), particularly where infertility is associated with adenomyosis.

The present inventors unexpectedly discovered that administration of HDACI, derivatives and/or salts thereof has a beneficial effect on pregnancy rates in patients suffering with adenomyosis associated infertility for example by aiding or enhancing implantation and/or by decreasing miscarriage rates in patents. It is contemplated within the scope of the present invention that HDACI may be selected from a group comprising medically approved or awaiting approval HDACI, derivative and/or salts thereof or commercially-available products.

In one aspect, there is disclosed a method of enhancing in vitro fertilization (IVF) in a subject suffering with adenomyosis associated infertility, the method comprising administering a therapeutically effective amount of HDACI, derivatives and/or salts thereof. It would be known to those of skill in the art that different HDACI are already used in medicine.

Histone deacetylases (HDACs) are a class of enzymes found in bacteria, fungi, plants and animals that remove the acetyl group from the ε-amino groups of lysine residues located in the NH2 terminal tails of core histones. There are 18 known human histone deacetylases, grouped into four classes based on the structure of their accessory domains. Class I includes HDAC1, HDAC2, HDAC3, and HDAC8 and have homology to yeast RPD3. HDAC4, HDAC5, HDAC7, and HDAC9 belong to class II and have homology to yeast HDA1. HDAC6 and HDAC10 contain two catalytic sites and are classified as class IIa, whereas HDAC11 has conserved residues in its catalytic center that are shared by both class I and class II deacetylases and is sometimes placed in class W.

TABLE 1 bellow shows a list of histone deacetylase enzymes (Seto E., et al., *Cold Spring Harb Perspect Biol.* 2014; 6(4)) which are all suitable for use in the methods of the present invention.

| Superfamily | Family | Class | Protein (*S. cerevisiae*) | Subclass | Protein (human) |
|---|---|---|---|---|---|
| Arginase/deacetylase superfamily | Histone deacetylase family | Class I | Rpd3, Hos1, Hos2, Hos3 | | HDAC1, HDAC2, HDAC3, HDAC8 |
| | | Class II | Hda1 | Class IIa | HDAC4, HDAC5, HDAC7, HDAC9 |
| | | | | Class IIb | HDAC6, HDAC10 |
| | | | | Class IV | HDAC11 |
| Deoxyhypusine synthase like NAD/FAD-binding domain superfamily | Sir2 regulator family | Class III | Sir2, Hst1, Hst2, Hst3, Hst4 | I | SIRT1, SIRT2 |
| | | | | II | SIRT3 |
| | | | | III | SIRT4 |
| | | | | IV | SIRT5, SIRT6, SIRT7 |

As used in the present invention, a therapeutically effective amount of HDACI can be delivered to a patient as part of a regimen.

As used herein the term "regimen" refers to a plan or a set of rules of different possible routs or modes of administration, preferably to achieve a therapeutically effective amount of HDACI in a patient. By way of non-limiting example, the regimen may vary depending on for example the type of patient to be treated, the severity or acuteness of the medical condition which may be associated with or causing the infertility such as adenomyosis, the number of times assisted fertilization such as standard IVF, has unsuccessfully been attempted, prior to the method of the present invention. By way of example, in a cohort of 20 patients who have had at least one negative result for pregnancy after embryo transfer—12 of these 20 patients having already experiences two or more negative result for pregnancy after embryo transfer—85% of them became pregnant after treatment using the method of the present invention (17 from 20).

In some embodiments, the subject suffering with adenomyosis associated infertility has had at least one negative result for pregnancy after standard IVF. In some embodiments, the subject suffering with adenomyosis associated infertility has had two or more negative result for pregnancy after standard IVF. In some embodiments, the subject suffering with adenomyosis associated infertility has had three or more negative result for pregnancy after standard IVF.

In some embodiments, there is provided a method of enhancing in vitro fertilization (IVF) in a patient suffering with adenomyosis associated infertility, the method comprising a regimen of administration of HDACI, derivatives and/or salts thereof.

It would be known to those of skill in the art that different regimens may be employed in the context of the present invention.

In some embodiments, the regimen of administration of HDACI, derivatives and/or salts thereof is carried out using methods known in the art.

By way of non-limiting example, the term administration should be understood to encompass intrauterine, intralesional, peroral, rectal, topical, parenteral, intramuscular, intravenous, transdermal, implantation or combinations thereof.

In some embodiments, the regimen of administration of HDACI, derivatives and/or salts thereof can be selected from the group consisting of intrauterine, intralesional, peroral, rectal, topical, parenteral, intramuscular, intravenous, transdermal, implantation or combinations thereof.

In some embodiments, the regimen of administration of HDACI, derivatives and/or salts thereof is carried out using intrauterine administration.

In some embodiments, the regimen of administration of HDACI, derivatives and/or salts thereof is carried out using intralesional administration. Examples of "intralesional administration" include injection or infusion.

In some embodiments, there is provided a method of enhancing in vitro fertilization (IVF) in a subject suffering with adenomyosis associated infertility, wherein the regimen comprises a combination of intralesional and peroral administration of HDACI, derivatives and/or salts thereof.

In some embodiments, the regimen comprises one or more intralesional administrations of HDACI, derivatives and/or salts thereof. In some embodiments, the regimen comprises two or more intralesional administrations. In some embodiments, the regimen comprises three or more intralesional administrations. In some embodiments, the regimen comprises four or more intralesional administrations. In some embodiments the regimen comprises two intralesional administrations.

In some embodiments, the intralesional administration of HDACI, derivatives and/or salts thereof is carried out using methods known in the art.

In some embodiments, the intralesional administration is carried out using hysteroscopy.

In some embodiments, the intralesional administration is carried out using hysteroscopy or transvaginal ultrasound-guided needle.

In some embodiments, the intralesional administration is carried out using transvaginal ultrasound-guided needle selected from the group comprising 18G, 21G, 23G, 25G or 30G.

It will be appreciated by those skilled in the art that the amount of HDACI, derivatives and/or salts thereof required in the present methods will vary with the nature or severity of the condition being treated, the type of the adenomyotic lesions, the age, weight and the overall condition of the patient, and will be ultimately at the discretion of the attendant physician.

In general however, dose of HDACI, derivatives and/or salts thereof employed in the present methods will typically be in the range of about 2 to about 1000 mg/ml per administration, dependent upon the route of administration.

The desired dose may conveniently be presented in a single dose or as divided doses administered at appropriate intervals, for example as two, three, four or more sub-doses per day or per administration.

In some embodiments, for intralesional administration a dose will typically be in the range of about 1 to 500 mg/ml, about 5 to 250 mg/ml, about 10 to 200 mg/ml, about 20 to 150 mg/ml, about 50 to 100 mg/ml per administration. In some embodiment the dose of intralesional administration is 100 mg/ml per administration.

HDACIs suitable for intralesional administration such as injectable use include, but is not limited to, sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, sterile water, ethanol, polyol (for example, glycerol, propylene glycol and liquid polyethylene glycol and the like), suitable mixtures thereof, and vegetable oils. The proper fluidity can be maintained, for example, by the use of a coating such as lecithin, by the maintenance of the required particle size in the case of a dispersion, and by the use of surfactants. The preventions of the action of microorganisms can be brought about by various antibacterial and antifungal agents; for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate, and gelatin.

Sterile injectable solutions are prepared by incorporating the active material in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique, which yield a powder of the active ingredient plus any additional desired ingredient from previously sterile-filtered solution thereof.

In some embodiments, the regimen comprises one or more peroral administrations of HDACI, derivatives and/or salts thereof.

In some embodiments, the regimen comprises two or more peroral administrations. In some embodiments, the regimen comprises three or more intralesional administrations.

In some embodiments, the regimen comprises four or more peroral administrations.

In some embodiments, the regimen comprises two peroral administrations of HDACI, derivatives and/or salts thereof.

In some embodiments, for peroral administration, a daily dose will typically be within the range of about 10 to 1500 mg, about 50 to 1250 mg, about 100 to 1000 mg, about 200 to 750 mg. In some embodiments, the oral administration daily dose is 1000 mg.

The inventors found that HDACIs may be conveniently administered to a subject by the peroral route, particularly in the form of a tablet or capsule (e.g. a tablet). Moreover, the inventors found that the particular dosage regimes contemplated in the invention are particularly suited to oral administration in the form of a tablet or capsule that is formulated such that the release of compounds used in the invention e.g. HDAI, from said tablet or capsule after oral administration is delayed.

As used herein, references to HDACIs or formulations comprising HDACIs allowing for delayed or controlled released will be understood by those skilled in the art. In this regard, it will be understood that as used here in the terms "delayed" and "controlled" may be used interchangeably.

In some embodiments, there is provided a method of enhancing in vitro fertilization (IVF) in a subject suffering with adenomyosis associated infertility, the method comprising a regimen of:

a. a first intralesional administration of HDACI, derivatives and/or salts thereof;

b. a first peroral administration of HDACI, derivatives and/or salts thereof lasting for about one month after step a):

c. a second intralesional administration of HDACI, derivatives and/or salts thereof; and d. a second peroral administration of HDACI, derivatives and/or salts thereof lasting for about one month after step c); followed by e. standard IVF.

It would be understood by those of skill in the art that the timing of initiation of the first peroral administration following the first intralesional administration, would vary depending on different factors. In some embodiments the first intralesional administration can be followed by the first peroral administration within 0.5 hours after the first intralesional administration, within 1 hour after the first intralesional administration, within 2 hours after the first intralesional administration, within 3 hours after the first intralesional administration, within 4 hours after the first intralesional administration, within 5 hours after the first intralesional administration, within 6 hours after the first intralesional administration, within 7 hours after the first intralesional administration, within 8 hours after the first intralesional administration, within 9 hours after the first intralesional administration, within 10 hours after the first intralesional administration, within 11 hours after the first intralesional administration, within 12 hours after the first intralesional administration, within 13 hours after the first intralesional administration, within 14 hours after the first intralesional administration, within 15 hours after the first intralesional administration, within 20 hours after the first intralesional administration, within 24 hours after the first intralesional administration or more.

It would be understood by those of skill in the art that the duration of the first peroral administration after the first intralesional administration, would vary depending on different factors. In some embodiments, the first peroral administration can last for about 1 week after the first intralesional administration. In some embodiments, the first peroral administration can last for about 2 weeks after the first intralesional administration. In some embodiments, the first peroral administration can last for about 3 weeks after the first intralesional administration. In some embodiments, the first peroral administration can last for about 4 weeks after the first intralesional administration. In some embodiments, the first peroral administration can last for about 5 weeks after the first intralesional administration. In some embodiments, the first peroral administration can last for about 6 weeks after the first intralesional administration or more.

In some embodiments, the first peroral administration lasts for about 1 (one) month after the first intralesional administration.

It would be understood by those of skill in the art that the timing of initiation of the second peroral administration following the second intralesional administration, would vary depending on different factors. In some embodiments the first intralesional administration can be followed by the second peroral administration within 0.5 hours after the second intralesional administration, within 1 hour after the second intralesional administration, within 2 hours after the second intralesional administration, within 3 hours after the second intralesional administration, within 4 hours after the second intralesional administration, within 5 hours after the second intralesional administration, within 6 hours after the second intralesional administration, within 7 hours after the second intralesional administration, within 8 hours after the second intralesional administration, within 9 hours after the second intralesional administration, within 10 hours after the second intralesional administration, within 11 hours after the second intralesional administration, within 12 hours after the second intralesional administration, within 13 hours after the second intralesional administration, within 14 hours after the second intralesional administration, within 15 hours after the second intralesional administration, within 20 hours after the second intralesional administration, within 24 hours after the second intralesional administration or more.

It would be understood by those of skill in the art that the duration of the second peroral administration after the second intralesional administration, would vary depending on different factors. In some embodiments, the second peroral administration can last for about 1 week after the second intralesional administration. In some embodiments, the second peroral administration can last for about 2 weeks after the second intralesional administration. In some embodiments, the second peroral administration can last for about 3 weeks after the second intralesional administration. In some embodiments, the second peroral administration can last for about 4 weeks after the second intralesional administration. In some embodiments, the second peroral administration can last for about 5 weeks after the second intralesional administration. In some embodiments, the second peroral administration can last for about 6 weeks after the second intralesional administration or more. In some embodiments, the second peroral administration can last for about 7 weeks after the second intralesional administration or more. In some embodiments, the second peroral administration can last for about 8 weeks after the second intralesional administration or more. In some embodiments, the second peroral administration can last for about 9 weeks after the second intralesional administration or more. In some embodiments, the second peroral administration can last for about 10 weeks after the second intralesional administration or more. In some embodiments, the second peroral administration can last for about 11 weeks after the second intralesional administration or more. In some embodiments, the second peroral administration can last for about 12 weeks after the second intralesional administration or more. In some embodiments, the second peroral administration can last for about 13 weeks after the second intralesional administration or more. In some embodiments, the second peroral administration can last for about 14 weeks after the second intralesional administration or more. In some embodiments, the second peroral administration can last for about 15 weeks after the second intralesional administration or more.

In some embodiments, the second peroral administration lasts for about 3 (three) month after the second intralesional administration.

In some embodiments, there is provided a method of enhancing in vitro fertilization (IVF) in a subject suffering with adenomyosis associated infertility, the method comprising a regimen of intralesional and peroral administration of HDACI, derivative and/or salts thereof which leads to regression of adenomyosis lesions.

Regimens of the present invention give rise to surprising advantages in terms of implantation and miscarriage in patients with infertility problems such as those suffering with adenomyosis associated infertility.

In some embodiments, there is provided a method of enhancing in vitro fertilization (IVF) in a subject suffering with adenomyosis associated infertility, the method comprising a regimen of intralesional administration and peroral intake of HDACI, derivative and/or salts thereof, where the frequency of occurrence of the lesions is reduced by at least 0.5%, at least 1%, at least 5%, at least 10%, at least 20%, at least 30%, at least 40%, at least 50%, at least 60%, at least 70%, at least 80%, at least 90%, at least 100%, at least 120%, at least 135%, at least 140%, at least 150, at least 160%, at least 170%, at least 180%, at least 190%, at least 200%, at least 210%, at least 220%, at least 230%, at least 250% or more.

In some embodiments, the present method alters the size of the adenomyosis lesions. As used herein the term "size" refers to the diameter, circumference, contour or surface of the adenomyosis lesion. In some embodiments, there is provided a method for treating adenomyosis, the method comprising a regimen of intralesional administration and peroral intake of HDACI, derivative and/or salts thereof, where the size e.g. diameter, circumference, contour or surface, of the lesions is reduced.

In some embodiments, there is provided a method of enhancing in vitro fertilization (IVF) in a subject suffering with adenomyosis associated infertility, the method comprising a regimen of intralesional and peroral administration of HDACI, derivative and/or salts thereof, where the lesions are reduced by at least 0.5%, at least 1%, at least 5%, at least 10%, at least 20%, at least 30%, at least 40%, at least 50%, at least 60%, at least 70%, at least 80%, at least 90%, at least 100%, at least 120%, at least 135%, at least 140%, at least 150, at least 160%, at least 170%, at least 180%, at least 190%, at least 200%, at least 210%, at least 220%, at least 230%, at least 250% or more.

In some embodiments, there is provided a method of enhancing in vitro fertilization (IVF) in a subject suffering with adenomyosis associated infertility, where the method leads to at least 50% remission of adenomyosis, at least 55% remission of adenomyosis, at least 60% remission of adenomyosis, at least 65% remission of adenomyosis, at least 70% remission of adenomyosis, at least 75% remission of adenomyosis, at least 80% remission of adenomyosis, at least 81% remission of adenomyosis, 82%, 83%, 84%, 85%, 86%, 87%, 88%, 89%, 90%, 91%, 92%, 93%, 94%, 95%, 96%, 97%, 98%, 99% or 100% remission of adenomyosis. In some embodiments, there is provided a method for treating adenomyosis, wherein the treatment leads to full remission of adenomyosis.

In some embodiments, there is provided a method of enhancing in vitro fertilization (IVF) in a subject suffering with adenomyosis associated infertility, wherein the method leads to an enhancement in embryo retention.

In some embodiments, there is provided a method of enhancing in vitro fertilization (IVF) in a subject suffering with adenomyosis associated infertility, wherein the method leads to an increase of success of conception following IVF.

In some embodiments, there is provided a method of enhancing in vitro fertilization (IVF) in a subject suffering with adenomyosis associated infertility, wherein the method leads to at least 0.5%, at least 1%, at least 2%, at least 3%, at least 4%, at least 5%, at least 6%, at least 7%, at least 8%, at least 9%, at least 10% or more, increase in a successful conception.

The method is also applicable for women wanting to improve their prospects of pregnancy through natural conception.

In some embodiments, there is provided a method of enhancing in vitro fertilization in a patient suffering with adenomyosis associated infertility, wherein the HDACI, derivative and/or salts thereof, comprises valproic acid (VPA), derivative and/or salts thereof. In some embodiments, the VPA salt is sodium valproate.

In some embodiments, the intralesional administration dose of VPA, derivative and/or salt thereof will typically be in the range of about 1 to 500 mg/ml, about 5 to 250 mg/ml, about 10 to 200 mg/ml, about 20 to 150 mg/ml, about 50 to 100 mg/ml per intralesional administration. In some embodiment the VPA intralesional administration dose is 100 mg/ml per administration. In some embodiments the intralesional administration dose of sodium valproate is 100 mg/ml.

In some embodiments, the oral administration daily dose of VPA, derivative and/or salt thereof will typically be within the range of about 10 to 1500 mg, about 50 to 1250 mg, about 100 to 1000 mg, about 200 to 750 mg. In some embodiments, the oral administration daily dose of VPA, derivative and/or salt thereof is 1000 mg. In some embodiments, the oral administration daily dose of sodium valproate is 1000 mg.

As used herein, the term "therapeutically effective amount" will be understood to refer to plasma levels of the relevant HDACI, derivative and/or a salt thereof, at which the relevant (i.e. normally associated) therapeutic effect of that HDACI will typically be observed. The term may refer to a range of plasma levels or to a specific plasma level.

In some embodiments, reference to a therapeutically effective amount of HDACI per millilitre (/ml) will be understood to refer to an amount per millilitre of plasma (i.e. blood plasma of the patient). As used herein, the reference to molar concentration will be understood to refer to a concentration in plasma (i.e. blood plasma of the patient).

In some embodiments, the patient has a plasma concentration of valproic acid, or a salt and/or metabolite thereof, that is below about 50 to about 170 $\mu$g/ml (such as e.g. below about 50, about 70, about 90, about 110, about 130, about 150, or about 170 $\mu$g/ml).

In some embodiments, the patient has a plasma concentration of valproic acid, or a salt and/or metabolite thereof, that is at least about 70 to about 700 $\mu$M (such as e.g. at least about 70, about 140, about 210, about 280, about 350, about 420, about 490, about 560, about 630 or about 700 $\mu$M).

In some embodiments, the patient has a plasma concentration of valproic acid, or a salt and/or metabolite thereof, that is below about 350 to about 1200 $\mu$M (such as e.g. below about 350, about 490, about 630, about 770, about 910, about 1050, or about 1190 $\mu$M).

For the avoidance of doubt, the skilled person will understand that references to certain maximum amounts and concentrations in plasma may also require a minimum of a therapeutically effective amount in the plasma.

In particular, the skilled person will understand that references to certain maximum (i.e. where values are indicated as being "below") and minimum (i.e. where values are indicated as being "at least") amount and/or concentrations in plasma may be combined to form ranges (i.e. wherein the amount in plasma is in a range that is from the minimum value to the maximum value).

As used herein, the terms "enhancing", "improved rate", "encouraging", "aiding", "increased rate", etc., as used herein in connection with for example in vitro fertilization (IVF) or effects on implantation, pregnancy or lesions, include any measurable improvement or increase in frequency of occurrence of implantation or pregnancy in an individual or group of patients treated in accordance with the present invention, for example when compared with the level or frequency of occurrence of implantation or pregnancy in one or more non-treated patients or when compared to the level or frequency of occurrence of implantation or pregnancy in the same patient observed at an earlier time point (e. g. comparison with a "base line" level). Preferably the enhancing will be a statistically significant one, preferably with a probability (p) value of <0.05. Methods of determining the statistical significance of results are well known and documented in the art and any appropriate method may be used. In some embodiments the methods of determining the statistical significance of results include IBM SPSS Statistics software other statistical methods. In some embodiments the enhancing is also represented in terms of percent (%).

As used herein the term "regression" means make less, bring down, lower, make smaller or lessen, for example, adenomyosis lesions. The term "regression" may be used interchangeably with the terms, "reduction", "decrease" or "reduce". In some embodiment, regression is used to provide an indication of the extent by which, for example, adenomyosis lesions are altered in terms of, for example, frequency of occurrence, distribution, colour, degree, intencity, diameter or size. The terms "regression", "decreased", "decreasing", "reduction", "reducing", etc. as used herein in connection with adenomyosis lesion or miscarriage, refer to any measurable decrease or reduction in an individual patient or group of patients treated in accordance with the present invention, for example when compared with the frequency of occurrence of miscarriage in one or more non-treated patients or when compared to the level or frequency of occurrence of adenomyosis lesions or miscarriage in the same subject observed at an earlier time point (e. g. comparison with a "base line" level). Preferably the decrease will be a statistically significant one, preferably with a probability (p) value of <0.05. Methods of determining the statistical significance of results are well known and documented in the art and any appropriate method may be used. In some embodiments the methods of determining the statistical significance of results include IBM SPSS Statistics software other statistical methods. In some embodiments the decrease is also represented in terms of percent (%).

Miscarriage is defined as expulsion of the fetus before it is capable of independent survival. Early miscarriage refers to those miscarriages that occur in the first month of foetal development. The methods and uses of the present invention have particular utility in reducing the levels of early miscarriage.

In some embodiments, the present method alters the frequency of occurrence of adenomyosis lesions.

As used herein, the term "alter" means affect or change such as for example, enhance when used in connection with in vitro fertilization (IVF) or regress when used in connection with adenomyosis lesions, when compared to the same patient observed at a different time point (e. g. comparison with a "base line" level). It would be readily understood by the skilled person that the term "time point" as used herein means, before, during and/or after treatment of the patient using method of the present invention.

In some embodiments, the present method reduces the frequency of occurrence of the adenomyosis lesions.

Without wishing to be bound by theory, adenomyotic lesions may be characterised with dense round structure and/or pale colour which are readily distinguishable for example by ultrasonography (ultrasound), from normal healthy endometrium. In the case of diffuse adenomyotic lesions or a combination of diffuse lesions and dense round structure lesions, although ultrasonography may be relied upon to distinguish these lesions from normal healthy endometrium, other imaging techniques such as pelvic imaging, MRI, endoscopy, or physical examination may be relied upon. Different imaging techniques for characterizing adenomyosis lesions or diagnosis of adenomyosis would be familiar to those of skill in the art and the skilled person would be able to select the appropriate technique in order to determine the type and size of adenomyotic lesions.

In some embodiments, ultrasound imaging technique is used to determine adenomyotic lesions.

In some embodiments, ultrasound imaging technique is used to determine the type and size of the adenomyotic lesions before the method.

In some embodiments, ultrasound imaging technique is used to determine the type and size of the adenomyotic lesions during the method.

In some embodiments, ultrasound imaging technique is used to determine the type and size of the adenomyotic lesions after the method.

In some embodiments, ultrasound imaging technique is used to determine alterations in the adenomyotic lesions as a consequence of the method.

As used herein the term "frequency of occurrence" refers to an adenomyosis lesion which is characterised or assessed in terms of location, dimension, number or structure e.g. by means of 2D/3D ultrasound, MRI or endoscope, when compared to the same patient observed at an earlier time point (e. g. comparison with a "base line" level).

Transvaginal Sonography (TVS) Presentation and Diagnosis

In some embodiments, signs suggestive of the presence of endometrial tissue within the myometrium can be observed by TVS. Findings suggestive of adenomyotic lesion: oval, non-capsulated area in the myometrium, heteroschogenic, variable in size. Main difference from uterine fibroids: no posterior cone of shadow and no hyperechoic. Colour Doppler typically reveals increased vascularity; not peripheral like in myomas, but central (Ryan K. et al., *RadioGraphics* 2018 38:5, 1576-1589; Fedele L et al., *Fertil Steril* 1992; 58: 94-7; Atri M. et al., *Radiology* 2000; 215: 783-90; Reinhold C. et al., *Radiographics* 1999; 19: S147-60).

In some embodiment, diagnosis of adenomyosis is with uterine leiomyomas (with a very high coexistence). Colour Doppler is very helpful in differentiating from uterine leiomyoma—when a typical intense vascularization is displayed perpendicular to the endometrium, is suggestive of adenomyiosis. A characteristic "Swiss cheese" appearance is sometimes observed, with many small, irregular cystic spaces (5-7 mm) within the myometrium (Agostinho L. et al., *Insights Imaging.* 2017; 8(6):549-556. doi:10.1007/s13244-017-0576-z).

Pathophysiology

Examples of adenomyosis pathophysiology are:
Sex Steroid Hormone Changes:
 Increased: Local hyperestrogenism; Increased uterine peristalsis due to estrogen excess and Increase of estrogen receptor (ER) and Bcl-2 gene expression;
 Decreased: Progesterone receptor expression
Proliferation and Fibrosis:
 Increased expression of: TGF-β-transforming growth factor β family; Myostatin, follistatin and activin A; and Trichostatin A.
Inflammation:
 Increased expression in the adenomyotic nodules of: Cytokines, Interleukins; and Prostaglandins.
Neuroangiogenesis:
 Increased expression of: Nerve growth factor (NGF); MMP-2, MMP-9 (metalloproteinases), and VEGF; and Endothelial nitric oxide synthase (eNOS);
 Down-regulation: Gene associated with Retinoid-Interferon-induced Mortality-1 (GRIM-1).

Etiology and Pathogenesis

One of the hypotheses considers hyper-estrogenic as the leading factor and adenomyosis as a consequence of the mechanism of tissue injury and repair (TIAR) (Leyendecker, G. & Wildt, L. 2011 *Hormone Molecular Biology and Clinical Investigation,* 5(2), pp. 125-142). The uterus is constantly active throughout the reproductive period. The molecular mechanisms associated with mechanical strain, injury, and repair display a pattern that is quite similar in different tissues and involves the expression of the P450 aromatase and the local production of estrogen.

Although the etiology and pathogenesis of adenomyiosis remain unclear, data from published research suggest that genetic and epigenetic abnormalities may play a crucial part in the pathogenesis of adenomyosis (Vannuccini S., et al., *Reprod Biomed Online* 2017; 35: 592-601).

Various abnormalities have been linked to adenomyiosis, including abnormalities of inflammatory response, cytokine/chemokine expression, protease activation, autophagy, immunosuppressive microenvironment and epigenetic regulation.

HDAC Inhibitors (HDACI or HDACIs)

Without wishing to be bound by theory, the effects of histone deacetylase inhibitors (HDACI or HDACIs) on normal endometrial stromal cells is generally weak or at best marginal (Kawano, Y., et al., 2011 *Human Reproduction,* 26(9), 2486-2498. doi:10.1093/humrep/der203; Chateauvieux S., *J Biomed Biotechnology* 2010; 2010:1-18).

HDACIs approved for use in medicine can be employed in the methods of the present invention or the uses provided or described here.

Few HDACI have been approved by the different health authorities and each one of these or combinations of these may be used in the methods of the present invention, as follows: vorinostat (Zolinza®; Merck) for the treatment of refractory cutaneous T-cell lymphoma (CTCL) (Duvic 2007 *Blood* 109: 31-39); romidepsin (Istodax®) for the treatment of CTCL and peripheral T-cell lymphoma (PTCL) (Vander Molen 2011 *J Antibiot* (Tokyo) 64: 525-531) and belinostat (Beleodaq®) for the treatment of PTCL (West 2014 *J Clin Invest* 124: 30-39). In early 2015 oral panobino stat (Farydak®) has been approved by the FDA, as combination therapy with bortezomib and dexamethasone in patients with recurrent multiple myeloma (Garnock-Jones K P (2015) *Drugs*. 75: 695-704). Again, in January 2015 an orally available small-molecule benzamide HDAC1,2,3 and 10 inhibitor, chidamide (Epidaza®) has been approved by the Chinese FDA for the treatment of colorectal and lung cancer, as well as for the treatment of relapsed or refractory PTCL (Ruolan Gu, (2015) *Journal of Chromatography*, 1000: 181-186). HDACIs are mostly studied as anticancer agents, neurological disorders, inflammatory processes and viral infections (Dinarello 2010 *Cell* 140: 935-950; Gray 2011 *Epigenomics* 3: 431-450; Giannini 2012 *Future Med Chem* 4: 1439-60).

Valproic acid (VPA) has also been approved for example as monotherapy and adjunctive therapy in the treatment of patients with complex partial seizures that occur either in isolation or in association with other types of seizures. VPA, promotes histone acetylation, which inhibits histone acetylation in the promoter region of the CYP19 gene, leading to suppression of expression (Chen et al., 2015 *International J. Molecular Medicine*, 36: 725-732). In some embodiments, there is provided a method of enhancing in vitro fertilization in a patient suffering with adenomyosis associated infertility, wherein the HDACI, derivative and/or salts thereof, comprises valproic acid (VPA), derivative and/or salts thereof. In some embodiments, the VPA salt is sodium valproate.

Commercially-available products containing valproic acid and/or sodium valproate, or prodrugs thereof which are also contemplated in the present invention and include for example—Depakote® (AbbVie Inc.), Absenor® (Orion Corporation), Convulex® (Pfizer), Convulex® CR, Depakene®/Depakine®/Depalept®/Deprakine® (AbbVie Inc./Sanofi Aventis), Depakine Chrono® (Sanofi), Depakene-R® (Kyowa Hakko Kogyo), Selenica-R® (Kowa), Encorate (Sun Pharmaceuticals India), Encorate Chrono® (Sun Pharmaceuticals), Epival (Abbott Laboratories), Epilim® (Sanofi), Epilim Chronospheres® modified release granules, Epilim Chrono Controlled® release tablets, Epilim Chrono® Prolonged release tablets, Stavzor® (Noven Pharmaceuticals), Valcote® (Abbott Laboratories), Valpakine® (Sanofi Aventis), Depamide® (Sanofi-Avetis), Dipexil-R® (Bial), Eliaxim (Bial), Sodium Valproate® Sandoz Tablets (Sanofi), Valpro® Tablets (Alphapharm), Valproate Winthrop® Tablets (Sanofi), Valprease® (Sigma), Epilim EC® modified release tablets (Sanofi-Aventis), Oriept® (Wockhardt), Epilim Chrono® (Sanofi) (1:2.3 ratio of valproic acid and sodium valproate), Epilim EC200® (Sanofi), Valprol CR® (Intas Pharmaceutical), Episenta® prolonged release (Beacon), Valproic Acid® capsules, USP® (Teva), Stavzor® (Noven), Orfiril® (Desitin Pharmaceuticals).

Commercially-available products containing valproic acid and/or sodium valproate, or prodrugs thereof which are also contemplated in the present invention, are contemplated in the present invention to include generic version of the above-mentioned agents, which may be sold/marketed under an altogether different name.

HDACI Combination Treatments

HDACIs can be administered in the present methods in combination with (e.g. in a combined formulation with) other therapeutic agents for example agents that are useful in adenomyosis associated infertility.

Unless otherwise stated or apparent from the context (e.g. when discussed in reference to a specific formulation or administration regimen), references to the dose of HDACI, derivatives and/or salts thereof, according to the invention (e.g. the dose of valproic acid derivatives and/or salts thereof such as sodium valproate) will be understood to refer to the dose of valproic acid (i.e. the dose of valproic acid itself, or the effective (i.e. equivalent) dose of valproic acid when administered in the form that includes or consists of one or more salt thereof.

In some embodiments, the formulation further comprises one or more (e.g. one) other therapeutic agents that are useful in the treating or preventing adenomyosis associated lesions and/or adenomyosis associated infertility. In such embodiments, the HDACIs may be provided in admixture with one or more other therapeutic agent.

In some embodiments, HDACIs may be administered and/or formulated in combination with: one or more anti-platelet agents, including but not limited to aspirin, persantin, ticagrelor and clopidogrel; one or more anticoagulant agents, such as heparin, low molecular weight heparin (LMWH), warfarin, anisindione, phenindone, bishydroxycoumarin, bivalirudin, eptifibatid; one or more vasodilators such as nitriles (for example, amylnitrile, nitroglycerin, sodium nitrile, isosorbide dinitrate), papaverine, nicotinic acid and cyclandelate. One or more agents preventing cardiovascular events such as, but not limited to statins, beta blockers, angiotensin converting enzyme inhibitors, angiotensin II receptor antagonists or diuretics; and/or one or more anti-inflammatory agents including steroids and NSAIDs (including but not limited to aspirin, ibuprofen, naproxen and diclofenac); one or more thrombolytic agents selected from, for example, recombinant t-PA, prourokinase, urokinase or streptokinase.

In some embodiments, there is provided a histone deacetylase inhibitor (HDACI), derivatives and/or salts thereof for use in enhancing in vitro fertilization (IVF) in a subject suffering with adenomyosis associated infertility.

In some embodiments, there is provided a HDACI, derivatives and/or salts thereof for use in enhancing in vitro fertilization (IVF), wherein the use described here comprises a therapeutically effective amount of said HDACI, derivatives and/or salts thereof.

In some embodiments, there is provided a HDACI, derivatives and/or salts thereof for use in enhancing in vitro fertilization (IVF), wherein the therapeutically effective amount of said HDACI, derivatives and/or salts thereof is achieved by a regimen of HDACI, derivatives and/or salts thereof.

In some embodiments, there is provided a HDACI, derivatives and/or salts thereof for use in enhancing in vitro fertilization (IVF) according, wherein the regimen described here comprises a combination of intralesional and peroral use of HDACI, derivatives and/or salts thereof.

In some embodiments, there is provided a HDACI, derivatives and/or salts thereof for use in enhancing in vitro fertilization (IVF), wherein the intralesional use described here comprises a dose of HDACI, derivatives and/or salts thereof in the range of about 1 to 500 mg/ml, about 5 to 250 mg/ml, about 10 to 200 mg/ml, about 20 to 150 mg/ml, about 50 to 100 mg/ml per use.

In some embodiments, there is provided a HDACI, derivatives and/or salts thereof for use in enhancing in vitro fertilization (IVF), wherein the peroral use described here comprises a daily dose of HDACI, derivatives and/or salts thereof in the range of about 10 to 1500 mg, about 50 to 1250 mg, about 100 to 1000 mg, about 200 to 750 mg.

In some embodiments, there is provided a HDACI, derivatives and/or salts thereof for use in enhancing in vitro fertilization (IVF), wherein the use described here leads to regression of adenomyosis lesions or reduction in the frequency of occurrence of the adenomyosis lesions.

In some embodiments, there is provided a HDACI, derivatives and/or salts thereof for use in enhancing in vitro fertilization (IVF), wherein where the frequency of occurrence of the lesions is reduced by at least 0.5%, at least 1%, at least 5%, at least 10%, at least 20%, at least 30%, at least 40%, at least 50%, at least 60%, at least 70%, at least 80%, at least 90%, at least 100%, at least 120%, at least 135%, at least 140%, at least 150, at least 160%, at least 170%, at least 180%, at least 190%, at least 200%, at least 210%, at least 220%, at least 230%, at least 250% or more.

In some embodiments, there is provided a HDACI, derivatives and/or salts thereof for use in enhancing in vitro fertilization (IVF), wherein the use alters the size of the adenomyosis lesions and/or reduction in the size of the adenomyosis lesions.

In some embodiments, there is provided a HDACI, derivatives and/or salts thereof for use in enhancing in vitro fertilization (IVF), wherein the size of the adenomyosis lesions is reduced by at least 0.5%, at least 1%, at least 5%, at least 10%, at least 20%, at least 30%, at least 40%, at least 50%, at least 60%, at least 70%, at least 80%, at least 90%, at least 100%, at least 120%, at least 135%, at least 140%, at least 150, at least 160%, at least 170%, at least 180%, at least 190%, at least 200%, at least 210%, at least 220%, at least 230%, at least 250% or more.

In some embodiments, there is provided a HDACI, derivatives and/or salts thereof for use in enhancing in vitro fertilization (IVF), wherein the use leads to at least 50% remission of adenomyosis, at least 55% remission of adenomyosis, at least 60% remission of adenomyosis, at least 65% remission of adenomyosis, at least 70% remission of adenomyosis, at least 75% remission of adenomyosis, at least 80% remission of adenomyosis, at least 81% remission of adenomyosis, 82%, 83%, 84%, 85%, 86%, 87%, 88%, 89%, 90%, 91%, 92%, 93%, 94%, 95%, 96%, 97%, 98%, 99% or 100% remission of adenomyosis.

In some embodiments, there is provided a HDACI, derivatives and/or salts thereof for use in enhancing in vitro fertilization (IVF), wherein the use described here leads to an enhancement in full-term embryo retention.

In some embodiments, there is provided a HDACI, derivatives and/or salts thereof for use in enhancing in vitro fertilization (IVF), wherein the use described here leads to at least 0.5%, at least 1%, at least 2%, at least 3%, at least 4%, at least 5%, at least 6%, at least 7%, at least 8%, at least 9%, at least 10% or more, increase in a successful conception.

In some embodiments, there is provided a HDACI, derivatives and/or salts thereof for use in enhancing in vitro fertilization (IVF), wherein the use described here leads to a statistically significant IFV.

In some embodiments, there is provided a HDACI, derivatives and/or salts thereof for use in enhancing in vitro fertilization (IVF), wherein the HDACI, derivative and/or salts thereof, comprises valproic acid (VPA), derivative and/or salts thereof.

In some embodiments, there is provided a HDACI, derivatives and/or salts thereof for use in enhancing in vitro fertilization (IVF), wherein the VPA salt is sodium valproate.

In order that the invention may be readily understood and put into practical effect, particular embodiments will now be described by way of the following non-limiting examples.

EXAMPLES

Example 1—Treatment Methods and Protocols

Treatment Regimen

Our treatment invention consists of two steps: intralesion application using hysteroscopy or transvaginal ultrasound-guided 18 G needle, and subsequent oral administration of valproic acid (or equal sodium salt) for a course of 3 months, followed by a second intralesion application and 1-month follow-up period before standard IVF.

Intralesional Application

A 100 mg/ml solution of sodium valproate for injection or infusion was prepared.

The final concentration we achieved after dilution with 0.9% sterile solution of NaCl is 5 mg/ml (eq. of 4.33 mg valproic acid) in total volume of 3.8 ml. This solution is drawn in 5 ml Luer lock syringe and administrated in the lesion(s) through special needle. We have used—OPU needle 18G, with echo tip and length at least 15 cm. The solution was administered in the ultrasound-guided manner in all visible lesions. The access was through the vagina.

The nominal amount of VPA applied in every lesion was between 1 ml for lesions below 1 cm and 2 ml for larger lesions. The VPA injection was applied in the centre of the lesion under ultrasound control.

The needle is introduced in the uterus via the vagina, and when the echo-positive tip has reached the centre of the lesion, the VPA solution is administered slowly. Intralesional application must start with the lesions located closest to the cavum uteri, in the so-called junctional zone, because these have the strongest influence on fertility. The procedure is performed under short-term intravenous anesthesia to ensure patient comfort and immobility during application; patients report no pain after anesthesia wear off.

Intralesional VPA application is repeated after 90 days (three months) in the same manner and in the same lesion locations as the first time.

Peroral Application

Approximately one hour after the first application every patient was given 60 tablets of Valproic acid and was advised to take 1 tablet in the morning and 1 tablet in the evening after meal starting with evening dose in day 1. The first oral dose must be taken between 9 h and 16 h after the end of intralesion application in order to achieve a steady state in patient plasma.

The course of oral administration of valproic acid was 3 months—between 2 intralesional applications.

Sodium valproate 500 mg prolonged-release tablets were used. The oral administration daily dose was fixed to a total of 1000 mg VPA, regardless of patient weight and age.

Safety and Tolerability

Pregnancy

Irrespective of their medical history of infertility and failed IVFs and/or spontaneous abortions, all patients were advised to use double contraception methods for the whole duration of the treatment course, because of the known teratogenic effects of VPA.

Liver Safety

VPA can have hepatotoxic effects in high doses, therefore every patient underwent safety lab blood tests before start of treatment as well as every 30 days after the first application till end of treatment. The safety lab panel included liver function tests (AST, ALT, LDH), as well as complete blood count. The safety lab results of all treated were in normal range throughout the treatment period, indicating excellent tolerability of the treatment regimen. Only 2 patients reported dizziness, and stopped oral VPA intake.

Example 2—Treatment Effect—Clinical Setting

Before first application of VPA, all lesions were assessed for location, dimensions and structure by means of 2D/3D ultrasound and/or MRI. This assessment was repeated before every intralesion application of VPA solution and was documented precisely. To eliminate operator bias, all TVUS scans of the same patient at baseline and after start of treatment were performed by the same specialist on the same ultrasound machine.

There were tested 37 women with adenomyosis and a history of infertility and/or abortions. The results we obtained demonstrate an extremely good response to treatment and beneficial effects surpassing expectations in every patient that was treated.

Some of the lesions disappeared completely and some of them were significantly reduced in size.

Table 2 below summarises treatment data for 37 women.

| Patient's initials | Age (years) | Life births prior trmt (y-1/n-0) | Abortions prior trmt (n-0/1-1/≥2-2 | Location of adenomyosis (1-diffuse/2-anterior wall/3-posterior wall/4-fundal) | Number unsuccessful IVF procedures before trmt (none-0, 1-2, more than 1-2) | Lesion diameter (a), cm/ before |
|---|---|---|---|---|---|---|
| TV | 51 | 1 | 2 | 1 | 1 | 1.5 |
| DR | 44 | 0 | 0 | 2 | 2 | 1.3 |
| SH | 40 | 0 | 1 | 2 | 1 | 0.7 |
| NG | 35 | 0 | 1 | 4 | 2 | 1.65 |
| HP | 39 | 0 | 0 | 2 | 0 | 2.9 |
| MS | 41 | 0 | 0 | 2 | 0 | 1.3 |
| MG | 47 | 0 | 0 | 4 | 2 | 1.6 |
| SV | 43 | 0 | 0 | 2 | 2 | 1.3 |
| FK | 46 | 1 | 2 | 1 | 2 | 3.2 |
| IG | 42 | 0 | 1 | 2 | 2 | 1.6 |
| TK | 42 | 0 | 0 | 2 | 2 | 3.3 |
| RN | 44 | 0 | 2 | 4 | 2 | 5.9 |
| DY | 46 | 0 | 0 | 2 | 2 | 3.4 |
| MS | 46 | 0 | 1 | 1 | 1 | 3.5 |
| KG | 42 | 1 | 2 | 2 | 2 | 1 |
| VL | 44 | 1 | 0 | 1 | 0 | 1 |
| NM | 35 | 0 | 2 | 2 | 2 | 1 |
| MI | 44 | 1 | 1 | 1 | 1 | 4 |
| UI | 50 | 0 | 0 | 2 | 1 | 1 |
| LR | 45 | 0 | 1 | 1 | 1 | 4.62 |
| VB | 43 | 0 | 0 | 2 | 1 | 1.98 |
| DSY | 46 | 0 | 1 | 3 | 2 | 2.94 |
| KM | 48 | 0 | 2 | 3 | 0 | 3 |
| GK | 43 | 0 | 2 | 2 | 1 | 3 |
| KH | 49 | 0 | 0 | 3 | 2 | 1 |
| ET | 38 | 0 | 2 | 1 | 1 | 1 |
| DT | 35 | 1 | 2 | 1 | 0 | 1 |
| RR | 46 | 0 | 0 | 1 | 1 | 1 |
| GD | 42 | 0 | 1 | 1 | 1 | 1 |
| YV | 40 | 0 | 0 | 1 | 1 | 1 |
| EZ | 36 | 1 | 1 | 1 | 1 | 3.06 |
| TT | 42 | 0 | 1 | 1 | 1 | 7 |
| AG | 44 | 0 | 0 | 1 | 1 | 2.4 |
| MA | 36 | 0 | 1 | 1 | 2 | 1.98 |
| NN | 48 | 0 | 0 | 1 | 1 | 1.2 |
| LD | | | | | 1 | 2 |
| DMD | | | | | 1 | 1.65 |

| Patient's initials | Lesion diameter (b), cm/ before | Lesion dimensions (a), cm/ after | Lesion dimensions (b), cm/ after | Reduction in diameter a (a before/a after) | Reduction in diameter b (b before/b after) | Pregnancy status life birth-1/ unsuccessful-0/no information yet-2) |
|---|---|---|---|---|---|---|
| TV | 1.3 | 0.8 | 1 | 46.67 | 23.08 | 2 |
| DR | 1.3 | 1.3 | 0.3 | 0.00 | 76.92 | 1 |
| SH | 0.8 | 0.5 | 0.5 | 28.57 | 37.50 | 0 |
| NG | 1.3 | 0 | 0 | 100.00 | 100.00 | 1 |
| HP | 2.4 | 2.3 | 2 | 20.69 | 16.67 | 1 |
| MS | 1.3 | 0.6 | 0.6 | 53.85 | 53.85 | 1 |
| MG | 1.6 | 1.15 | 1.15 | 28.13 | 28.13 | 2 |
| SV | 1.3 | 0.5 | 0.5 | 61.54 | 61.54 | 1 |
| FK | 3.2 | 3.5 | 3.2 | −9.38 | 0.00 | 0 |
| IG | 1.6 | 0 | 0 | 100.00 | 100.00 | 2 |
| TK | 3.1 | 2.75 | 2.75 | 16.67 | 11.29 | 1 |
| RN | 5.9 | 4.85 | 3.9 | 17.80 | 33.90 | 1 |
| DY | 3.1 | 2.66 | 3 | 21.76 | 3.23 | 2 |
| MS | 2.3 | 3.95 | 3.95 | −12.86 | −71.74 | 1 |
| KG | 1 | 1 | 1 | 0.00 | 0.00 | 1 |
| VL | 1 | 1 | 1 | 0.00 | 0.00 | 2 |
| NM | 1 | 1 | 1 | 0.00 | 0.00 | 2 |
| MI | 1.83 | 3.09 | 1.73 | 22.75 | 5.46 | 2 |

-continued

| | | | | | | |
|---|---|---|---|---|---|---|
| UI | 1 | 1 | 1 | 0.00 | 0.00 | 1 |
| LR | 3.63 | 1 | 1 | 78.35 | 72.45 | 2 |
| VB | 2 | 1.67 | 1.67 | 15.66 | 16.50 | 2 |
| DSY | 2.94 | 2 | 2 | 31.97 | 31.97 | 2 |
| KM | 3 | 3 | 3 | 0.00 | 0.00 | 2 |
| GK | 3 | 3 | 3 | 0.00 | 0.00 | 2 |
| KH | 1 | 0 | 0 | 100.00 | 100.00 | 1 |
| ET | 1 | 1 | 1 | 0.00 | 0.00 | 2 |
| DT | 1 | 0 | 0 | 100.00 | 100.00 | 2 |
| RR | 1 | 1 | 1 | 0.00 | 0.00 | 0 |
| GD | 1 | 1 | 1 | 0.00 | 0.00 | 1 |
| YV | 1 | 1 | 1 | 0.00 | 0.00 | 2 |
| EZ | 2.39 | 1.78 | 1.75 | 41.83 | 26.78 | 2 |
| TT | 5 | 1 | 1 | 85.71 | 80.00 | 1 |
| AG | 2.07 | 1 | 1 | 58.33 | 51.69 | 2 |
| MA | 1.98 | 0 | 0 | 100.00 | 100.00 | 2 |
| NN | 1.1 | 0 | 0 | 100.00 | 100.00 | 1 |
| LD | 2 | 1.2 | 1.2 | 40.00 | 40.00 | 1 |
| DMD | 1.65 | 0 | 0 | 100.00 | 100.00 | 1 |

Beneficial treatment effects are observed even after the first two months of oral VPA following intralesional VPA administration:

Ultrasound measurement of lesion dimensions shows significant reduction in size, up to 2-fold. Moreover, the echogenic structure of the lesions is changed, and they are visualized as brighter formations.

Colour Doppler confirms that the baseline increased central vascularity, characteristic of adenomyiotic lesions, is absent, indicating that blood flow to the lesions is terminated.

We used IBM SPSS Statistics software for all statistical evaluations below in Table 3—however other statistical methods which are known to the skilled person could also be used:

| Lesion diameter a | Lesion diameter b |
|---|---|
| Before treatment −2.21 ± 1.45 | Before treatment −1.97 ± 1.16 |
| After treatment −1.39 ± 1.22 | After treatment −1.30 ± 1.12 |
| Wilcoxon p < 0.001 | Wilcoxon p < 0.001 |

A significant reduction in lesion diameter was observed after treatment Table 4 below.

| | Reduction in diameter a (a before/a after) | Reduction in diameter b (b before/b after) | Lesion diameter (a), cm/ before | Lesion diameter (b), cm/ before |
|---|---|---|---|---|
| Mann-Whitney U | 133.000 | 110.000 | 120.000 | 124.500 |
| Wilcoxon W | 433.000 | 410.000 | 211.000 | 215.500 |
| Z | −.744 | −1.488 | −1.157 | −1.014 |
| Asymp. Sig. (2-tailed) | .457 | .137 | .247 | .311 |
| Exact Sig. [2*(1-tailed Sig.)] | .479[a] | .150[a] | .263[a] | .321[a] |

A trend was observed for greater reduction of diameter b in patients who gave birth following treatment using the methods described here as compared to those who did not FIG. 1. And Table 5 below.

| Area Under the Curve | | | | | |
|---|---|---|---|---|---|
| | | | | Asymptotic 95% Confidence Interval | |
| Test Result Variable(s) | Area | Std. Error[a] | Asymptotic Sig.[b] | Lower Bound | Upper Bound |
| Reduction in diameter a (a before/a after) | .574 | .102 | .464 | .374 | .774 |
| Reduction in diameter b (b before/b after) | .647 | .097 | .143 | .457 | .838 |

The extent of diameter reduction might therefore be used to predict the chance for successful pregnancy and birth in patients after treatment using the methods described here.

Every patient has had a follow-up visit every month after end of treatment for three months. For the duration of the follow-up period no progression of adenomyosis was observed.

One month after End of Treatment, a new IVF cycle is ready to be started, and pregnancies are followed up to full term birth. The results we have up to date show a stunning 85% pregnancy rate; 10 healthy full-term babies, and ongoing clinical pregnancies.

No pregnancy terminations, or uterine obstetric complications during C-Section.

Pregnancy rate was measured and is described below in Table 6:

| Binomial Test | | | | | | |
|---|---|---|---|---|---|---|
| | | Category | N | Observed Prop. | Test Prop. | Exact Sig. (1-tailed) |
| Pregnancy CODE | Group 1 | .00 | 24 | .6 | .8 | .023[a] |
| | Group 2 | 1.00 | 13 | .4 | | |
| | Total | | 37 | 1.0 | | |

Pregnancy rate using IVF, following treatment methods of the present invention or uses of HDACI, derivatives and/or salts thereof provided here, is significantly higher, i.e. it was enhanced, when compared to that of pregnancy rates typically reported in literature and observed in our clinic (data not published) for patients with this diagnosis i.e. adenomyosis associated infertility. This enhancement was completely unexpected to the present inventors and completely unexpected based on information available before the invention.

The disclosure illustratively described herein can suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed. It will also be appreciated that the method(s), use(s) and/or administrations(s) may be subject to numerous rearrangements, modifications and substitutions without departing from the scope of the present disclosure as set forth and defined by the following claims.

REFERENCES

McCluggage W G, Robboy S J: Mesenchymal uterine tumors, other than pure smooth muscle neoplasms, and adenomyosis. In: Robboy S J, Mutter G L, Prat J, et al.: (eds), editor. *Robboy's pathology of the female reproductive tract* (*second edition*) Churchill Livingstone Elsevier, London, UK; 2009; 427-56.

Peric H, Fraser I S: The symptomatology of adenomyosis. *Best Pract Res Clin Obstet Gynaecol.* 2006; 20(4):547-55.

Van den Bosch T, Van Schoubroeck D: Ultrasound diagnosis of endometriosis and adenomyosis: State of the art. *Best Pract Res Clin Obstet Gynaecol.* 2018; 51: 16-24.

Chen et al., 2015 *International J. Molecular Medicine,* 36: 725-732

FDA—Valprioc acid (VPA) approval—Reference ID: 3026475 https://www.accessdatafda.gov/drugsatfda_docs/label/2011/018081s046_18082 s0311b1.pdf Source: Seto E, Yoshida M. Erasers of histone acetylation: the histone deacetylase enzymes. Cold Spring Harb Perspect Biol. 2014; 6(4):a018713. Published 2014 Apr. 1. doi:10.1101/cshperspect.a018713

Ryan K. Cunningham, Mindy M. Horrow, Ryan J. Smith, and Joseph. Adenomyosis: A Sonographic Diagnosis Springer RadioGraphics 2018 38:5, 1576-1589

Fedele L, Bianchi S, Dorta M, Arcaini L, Zanotti F, Carinellis S. Transvaginal ultrasonography in the diagnosis of diffuse adenomyosis. Fertil Steril 1992; 58: 94-7

Atri M, Reinhold C, Mehio A R, Cahpman W B, Bret P M. Adenomyosis: US features with histologic correlation in an in-vitro study. Radiology 2000; 215: 783-90

Reinhold C, Tafazoli F, Mehio A, Wang L, Atri M, Siegelman E S, Rohoman L. Uterine adenomyosis: endovaginal U S and M R imaging features with histopathologic correlation. Radiographics 1999; 19: S147-60 (Review)

Agostinho L, Cruz R, Osorio F, Alves J, Setubal A, Guerra A. MRI for adenomyosis: a pictorial review. *Insights Imaging.* 2017; 8(6):549-556. doi:10.1007/s13244-017-0576-z Leyendecker, G. & Wildt, L. (2011). A new concept of endometriosis and adenomyosis: tissue injury and repair (TIAR). Hormone Molecular Biology and Clinical Investigation, 5(2), pp. 125-142. Retrieved 14 Feb. 2020, from doi:10.1515/HMBCI.2011.002

Vannuccini S, Tosti C, Carmona F, Huang S J, Chapron C, Guo S W, et al. Pathogenesis of adenomyosis: An update on molecular mechanisms. Reprod Biomed Online 2017; 35:592-601.

Kawano, Y., Nasu, K., Li, H., Tsuno, A., Abe, W., Takai, N., & Narahara, H. (2011). Application of the histone deacetylase inhibitors for the treatment of endometriosis: histone modifications as pathogenesis and novel therapeutic target. Human Reproduction, 26(9), 2486-2498. doi:10.1093/humrep/der203

Chateauvieux S, Morceau F, Dicato M, Diederich M. Molecular and therapeutic potential and toxicity of valproic acid. J Biomed Biotechnol 2010; 2010:1-18.

26

What is claimed is:

1. A method of enhancing in vitro fertilization (IVF) in a subject suffering with adenomyosis associated infertility, comprising: administering histone deacetylase inhibitor (HDACI), derivatives and/or salts thereof intralesionally to said subject prior to performing the IVF.

2. The method according to claim 1, wherein the administering comprises a therapeutically effective amount of said HDACI, derivatives and/or salts thereof.

3. The method according to claim 2, wherein the therapeutically effective amount of said HDACI, derivatives and/or salts thereof is achieved by a regimen of administering HDACI, derivatives and/or salts thereof.

4. The method according to claim 3, wherein the regimen further comprises peroral administration use of HDACI, derivatives and/or salts thereof.

5. The method according to claim 4, wherein the intralesional administration comprises a dose of HDACI, derivatives and/or salts thereof in the range of about 1 to 500 mg/ml per use.

6. The method according to claim 5, wherein the peroral administration comprises a daily dose of HDACI, derivatives and/or salts thereof in the range of about 10 to 1500 mg.

7. The method according to claim 1, wherein the administering leads to regression of adenomyosis lesions or reduction in the frequency of occurrence of the adenomyosis lesions.

8. The method according to claim 7, wherein the frequency of occurrence of the lesions is reduced by at least 0.5%.

9. The method according to claim 1, wherein the administering alters the size of the adenomyosis lesions and/or reduces the size of the adenomyosis lesions.

10. The method according to claim 9, wherein the size of the adenomyosis lesions is reduced by at least 0.5%.

11. The method according to claim 1, wherein the administering use leads to at least 50% remission of adenomyosis.

12. The method according to claim 1, wherein the method results in an enhancement in full-term embryo retention following the IVF.

13. The method according to claim 1, wherein the method results in at least 0.5% increase in a successful conception following the IVF.

14. The method according to claim 1, wherein the method results in a statistically significant enhancement of IFV success.

15. The method according to claim 1, wherein the HDACI, derivative and/or salts thereof, comprises valproic acid (VPA), derivative and/or salts thereof.

16. The method according to claim 15, wherein the VPA salt is sodium valproate.

17. The method according to claim 4, wherein the peroral administration lasts for about one week to about three months.

18. The method according to claim 1, wherein the administering HDACI, derivatives and/or salts thereof intralesionally comprises:

a first intralesional administration; and a second intralesional administration.

19. The method according to claim 18, further comprising administering HDACI, derivatives and/or salts thereof perorally between the first and second intralesional administrations.

20. The method according to claim 18, further comprising administering HDACI, derivatives and/or salts thereof perorally to said subject after the second intralesional administration.

* * * * *